United States Patent [19]

Sand

[11] Patent Number: 4,598,006

[45] Date of Patent: Jul. 1, 1986

[54] METHOD FOR IMPREGNATING A THERMOPLASTIC POLYMER

[75] Inventor: Michael L. Sand, Wilmington, Del.

[73] Assignee: Hercules Incorporated, Wilmington, Del.

[21] Appl. No.: 729,729

[22] Filed: May 2, 1985

[51] Int. Cl.$^4$ ............ A01N 17/08; A01N 9/00; C11B 9/00; C08K 3/18

[52] U.S. Cl. ............ 424/81; 424/78; 424/83; 523/102; 523/340; 523/347

[58] Field of Search ............ 523/102, 340, 347; 424/78, 81, 83

[56] References Cited

U.S. PATENT DOCUMENTS

| | | | |
|---|---|---|---|
| 3,553,296 | 1/1971 | Gaeckel | 523/102 |
| 3,775,227 | 11/1973 | Wilbert et al. | 523/102 |
| 3,804,796 | 4/1974 | Alexandre | 523/102 |
| 3,876,761 | 4/1975 | Shepherd | 428/78 |
| 4,051,159 | 9/1977 | Tsouchlas et al. | 523/102 |
| 4,095,031 | 6/1978 | Engel | 523/102 |
| 4,460,572 | 7/1984 | Derby et al. | 428/83 |
| 4,515,909 | 5/1985 | Sawano et al. | 523/102 |
| 4,521,541 | 6/1985 | Rutherford et al. | 521/114 |

FOREIGN PATENT DOCUMENTS 0020055  2/1981  Japan ............ 523/102

*Primary Examiner*—Herbert J. Lilling
*Attorney, Agent, or Firm*—Dale R. Lovercheck

[57] ABSTRACT

Disclosed is a method for impregnating a thermoplastic polymer with an impregnation material such as a fragrance or pest control agent or pharmaceutical composition. A thermoplastic polymer is impregnated by (1) dissolving an impregnation material such as a fragrance or pest control agent or pharmaceutical composition material in a volatile swelling agent maintained at or near supercritical conditions for the volatile swelling agent, (2) swelling the thermoplastic polymer by contacting it at or near supercritical conditions for the volatile swelling agent with the impregnation material-laden volatile swelling agent and then (3) reducing the pressure so that the volatile swelling agent diffuses out of the thus impregnated thermoplastic polymer.

9 Claims, No Drawings

METHOD FOR IMPREGNATING A THERMOPLASTIC POLYMER

FIELD OF THE INVENTION

This invention relates to the chemical art of polymers. In particular this invention relates to a method for making a thermoplastic polymer impregnated by material such as a fragrance or pest control agent or pharmaceutical composition.

BACKGROUND OF THE INVENTION

There is a desire for thermoplastic polymers which are impregnated with fragrance. For example, there is a desire for thermoplastic polymers which have fragrances, such as, perfume, flower, and fruit. The major difficulty with making such thermoplastic polymers centers around how the polymer can be impregnated with sufficient fragrance material without adversely affecting either the polymer or the fragrance material.

With some polymers impregnating can be achieved by soaking the polymer in the fragrance material or a solution containing the fragrance material. Soaking suffers from various drawbacks. Many polymers, notably thermoplastic polymers, are difficult to impregnate in this manner because of the slow rate, even at elevated temperatures, at which the fragrance materials diffuse into the polymer. And where elevated temperatures are required, there is a limitation placed on the choice of the fragrance material. The fragrance material cannot be heat sensitive.

Thermoplastic polymers are typically impregnated by introducing the fragrance material into a polymer melt prior to compression or injection molding. However, the high temperatures of the polymer melt can volatilize, degrade or otherwise adversely affect the fragrance material. U.S. Pat. No. 3,926,655 discloses a perfumed polyamide resin which is made by heating the polyamide resin until it is pourable and stirrable then blending a perfume oil therein. Similarly, U.S. Pat. No. 4,095,031 discloses perfumed polymers of ethylene and polar monomer made by heating the polymer until it is free-flowing and then blending a perfumed oil therein.

Nippon Oil, in Japanese unexamined application No. 59 152-151-A, discloses a fragrant thermoplastic resin packaging bag made from a sheet of soft resin with perfume and thermoplastic resin.

Nippon Oil, in Japanese unexamined application No. 59,124,941, discloses copolymer impregnated with 17% perfume kneaded with polyethylene to give pellets releasing fragrance.

U.S. Pat. No. 4,167,589 discloses a process for producing caffeine-free black tea which includes an aroma impregnation step. The process comprises first extracting the aromatic ic content from the tea with a supercritical solvent, separating the aromatic content from the solvent by reducing the pressure and extracting caffeine from the tea residue with a moist supercritical solvent. The aromatic content is then redissolved in a supercritical gas which is subsequently liquified. The tea residue is impregnated with the aromatic content by drawing off the subcritical gas from the liquid phase in the presence of the tea residue. The role of the liquified gas is to function as a precipitation medium for the aroma.

A need exists to impregnate other materials, such as, pharmaceuticals and pest control agents, into polymers for controlled release. Langer, in Chem. Eng. Commun., Vol. 6, pages 1–48 (1980), discloses the application of polymeric delivery systems in pharmaceutical, agricultural and fragrance uses. Langer, et al., in Biomaterials 2, October, 201–214 (1981) discloses some medical control release applications.

Peyron, in Parfums, Cosmetiques, Aromes, No. 55, 47–54, February-March (1984), discusses extraction of fragrance and pharmaceutical materials from natural products using carbon dioxide. Sims, in U.S. Pat. No. 4,281,171 (July 28, 1981), discloses that pyrethrins, which are useful as pest control agents, can be extracted from pyrethrum flowers with liquid carbon dioxide. Stahl, in Rev. Latinoamer. Quim. 11, 1–7 (1980), discloses that some alkaloids dissolve at 40° C. in supercritical carbon dioxide or nitrous oxide.

Grubb, U.S. Pat. No. 3,725,311; Wilbert, et al., U.S. Pat. No. 3,567,119; and Engel, U.S. Pat. No. 3,688,985 each discloses impregnated polymer systems.

SUMMARY OF THE INVENTION

A thermoplastic polymer is impregnated by dissolving a material in a volatile swelling agent maintained at or near supercritical conditions for the volatile swelling agent, swelling the thermoplastic polymer by contacting it with an impregnation material-laden volatile swelling agent at or near supercritical conditions for the volatile swelling agent, the impregnation material being a fragrance or pest control agent or pharmaceutical and then reducing the pressure so that the volatile swelling agent diffuses out of the thus impregnated thermoplastic polymer.

DETAILED DESCRIPTION OF THE PREFERRED EMBODIMENTS

In accordance with the method of the invention, a volatile swelling agent is used to impregnate thermoplastic polymers with an impregnation material. Preferred impregnation materials are fragrances, pest control agents and pharmaceuticals. The process for impregnating thermoplastic polymers is of use with fragrance, pest control agent and pharmaceutical impregnation materials which are soluble in a volatile swelling agent when the volatile swelling agent is maintained at or near supercritical conditions. Because of the lipophilic nature of the preferred swelling agents, typically, for the fragrance, pest control agent or pharmaceutical material to be soluble in the volatile swelling agent the impregnation material must be fat soluble. The impregnation materials must also have sufficiently low volatilities so that the impregnation materials remain in the thermoplastic polymer under the conditions employed to remove the volatile swelling agent.

Fragrances and other materials which can be dissolved in a volatile swelling agent at or near supercritical conditions can be included in this invention. Examples of other materials of practical importance are pheromones, pyrethrins and pharmaceutical compositions, such as, scopolamine.

Fragrances suitable for the present invention include substantially any of the conventional fragrance materials. These are complex mixtures of compounds including esters, ethers, aldehydes, alcohols, unsaturated hydrocarbons, terpenes such as are well known to those skilled in the fragrance art. Specific perfume fragrances are musk, rose oil, honeysuckle oil, pine oil, jasmine or oak musk, for example.

The fragrance, pest control agent or pharmaceutical impregnation material is dissolved by contacting it with a volatile swelling agent where the volatile swelling agent is maintained at or near supercritical conditions. Supercritical conditions are those where the volatile swelling agent is at a temperature above its critical temperature and at a pressure above its critical pressure. The critical temperature ($T_c$) is the temperature above which the swelling agent cannot be liquified at any pressure. The critical pressure ($P_c$) is the pressure required to condense the gas at $T_c$. Preferred conditions for dissolution are similar to those used for swelling the polymer. Typical solubilities of individual fragrance, pest control agent and pharmaceutical compounds are well known to those skilled in the art. Solubilities in supercritical fluids are generally known to be strongly dependent on temperature and pressure.

The swelling agent which is employed is chosen because of 1) its compatibility with the fragrance, pest control agent or pharmaceutical material and the thermoplastic polymer, 2) its low boiling and critical temperatures and its corresponding high volatilities and 3) its ability to swell the thermoplastic polymer. Representative swelling agents include carbon dioxide (vapor pressure of 1 atm at $-78.4°$ C., $P_c=1071$ psi, $T_c=31.0°$ C.); ethylene (B.P.$=-103.7°$ C., $P_c=742$ psi, $T_c=9.9°$ C.); and nitrous oxide (B.P.$=-88.5°$ C., $P_c=1052$ psi, $T_c=36.4°$ C.). Carbon dioxide is the preferred swelling agent because of its unusually high vapor pressure, its nonflammability and its low cost. Furthermore, because carbon dioxide is physiologically and environmentally safe and has no odor, any small amounts left in the thermoplastic polymer have no adverse effects. Nitrous oxide is also a preferred swelling agent for some impregnation materials.

The amount of fragrance, pest control agent or pharmaceutical impregnation material in the impregnated thermoplastic polymer can be controlled by the concentration of impregnation material in the volatile swelling agent. The greater the concentration of impregnation material in the volatile swelling agent, the greater the concentration of impregnation material in the final thermoplastic polymer. The concentration cannot be so great, however, that the behavior of the volatile swelling agent at or near supercritical conditions is adversely affected. In general, the concentration of impregnation material in volatile swelling agent is from about 0.1% to about 50% by weight, preferably about 10% to about 30% by weight for fragrance impregnation materials. Preferably from about 0.1% to about 3% by weight for pharmaceutical composition impregnation materials. The optimal concentration is readily determinable by one skilled in the art without undue experimentation following the teachings of this specification.

Any swellable thermoplastic polymer can be employed. Representative thermoplastic polymers include polypropylene, polyethylene, ethylene-vinyl acetate (EVA) copolymer and ethylene-ethyl acrylate copolymer.

The thermoplastic polymer is swollen by contacting it at or near supercritical conditions with the fragrance, pest control agent or pharmaceutical impregnation material-laden swelling agent. The contacting permits rapid diffusion of the impregnation material-laden swelling agent into the polymer. The greater the swelling the quicker and more complete the diffusion of the impregnation material. It has been found that the efficiency of the swelling is increased with increasing temperature at a constant pressure. There are, however, limits imposed on both the operating temperature and pressure.

The limits on the range of temperatures are purely practical and the optimal temperature for a specific application will be readily determinable by one skilled in the art after reading this specification. The lower limit is about 20° C. below the critical temperature of the swelling agent. In general, however, a temperature of at least 40° C. will be employed in order to ensure a convenient rate of swelling. The highest temperature which can be employed is set by the nature of the impregnation material and the thermoplastic polymer. The temperature cannot be so high that either is degraded or otherwise adversely affected. Consequently, the temperature employed will be from about 20° C. below the $T_c$ of the swelling agent up to about 100° C. with from about 40° C. to about 60° C. being preferred.

The limits on pressure are also determined by practical considerations and for a particular application, the optimal pressure will be readily determinable by one skilled in the art after reading this specification. The pressure of the swelling agent will typically be from about 500 psi to about 10,000 psi, with about 1000 psi to about 5000 psi being preferred. At low pressure the rate of swelling is slow. It is not economically feasible to swell at pressure greater than about 10,000 psi due to the cost of the equipment which would be required.

Another factor having bearing on the impregnation is the size and form of the polymeric matrix. The contacting can occur with a wide variety of forms, ranging from polymer flakes and pellets to the molded articles themselves. However, since the time required for the transfer of impregnation material depends on the ratio of external surface area to volume, a practical limit on the size of the molded article will exist.

The polymer is contacted with the impregnation material-laden swelling agent by means known in the art. Typical of such means are autoclaves.

After contacting, the volatile swelling agent is separated from the thermoplastic polymer leaving the impregnation material behind. Because of the volatility of the swelling agents employed, separation is easily accomplished merely by lowering the pressure.

It has been found, however, that if an autoclave containing perfumed molded products is vented too rapidly, the physical appearance of the product can be affected. Apart from the type of polymer, the extent to which the polymer is affected depends on many factors including the pressure, temperature, dimensions of the product, rate of venting and amount of impregnation material and supercritical fluid dissolved in the polymer. Consequently, the final product can be controlled by adjusting the above processing parameters.

Microvoids have been created in some molded polymer pieces by venting the swelling agent quickly. Furthermore, these microvoids tended not to form in the outer shell of the polymer piece. In some cases, phase separation of liquid fragrance from the polymer matrix to the surface of the polymer piece was observed after release of the swelling agent. The microvoids should be able to act as a reservoir for this liquid.

The observed structure of the product could favorably modify its retention and release characteristics for the impregnation material. The outer shell of the polymer piece should act as a large resistance to diffusion from the internal reservoir. An additional benefit, therefore, of using a volatile swelling agent at or near supercritical conditions is to create an impregnated product with fragrance, pest control agent or pharmaceutical release characteristics that are more constant with time than that obtained from a uniform polymer matrix.

The mode of demonstrating this invention is exemplified by the following examples of preferred specific embodiments. The invention is not limited to these specific examples.

EXAMPLE 1

Polymeric plaques having the composition shown in Table 1 and a surface to volume ratio of 10 cm$^{-1}$ are weighed and placed into a cylindrical, mesh basket. The basket is attached to the agitator shaft of a stirred autoclave. A tank containing compressed $CO_2$ is attached to a feed line and the autoclave is pumped to an intermediate pressure. The compressed gas feed line is then directed through a small vessel which contains a typical fragrance material composed of esters, alcohols, aldehydes and fixatives and the $CO_2$ becomes laden with the fragrance material, such as fragrant alcohols (for example, linalool), esters (for example, linalyl acetate), and aldehydes (for example, anisaldehyde) and blends thereof. The fragrance material-laden $CO_2$ is forced into the autoclave.

The results shown in Table I for fragrance under $N_2$ pressure are given as the amount of fragrance in the polymer product as a weight percent increase of polymer from starting polymer to swollen polymer when impregnated through immersion in fragrance under $N_2$ pressure. Results for the fragrance/$CO_2$ mixture are given as the amount of fragrance in the polymer product in the absence of any significant amount of residual $CO_2$ as a weight percent increase of polymer from starting polymer to swollen polymer when swollen under 92% carbon dioxide and 8% fragrance.

Table I shows impregnation of fragrance (by weight percent increase) into compression molded polymer plaques with $N_2$ or $CO_2$ at 25° C., 2500 psi for 2 hours for copolymers I-III. The weight ratio of $CO_2$:fragrance:polymer is 60:5:1.

TABLE I

| Polymer | Impregnation Medium | |
|---|---|---|
| | Fragrance under $N_2$ pressure | Fragrance/$CO_2$ mixture* |
| Copolymer I [ethylene-vinyl acetate (9% vinyl acetate)] | 0.74% | 0.89% |
| Copolymer II [ethylene-vinyl acetate (18% vinyl acetate)] | 4.37% | 6.49% |
| Copolymer III [ethylene-ethyl acrylate (18% ethyl acrylate)] | 3.80% | 4.86% |

*8 weight percent fragrance

EXAMPLE 2

Example 2 is carried out under the same conditions as Example 1 except that the contacting is carried out at 60° C. The weight ratio of $CO_2$:fragrance:polymer is 50:5:1. The composition of the polymer plaques and the percentage weight increase are show in Table II.

Table II shows the results of impregnation of fragrance (by weight percent increase) into compression molded polymer plaques with $N_2$ or $CO_2$ at 60° C. and 2500 psi for 2 hours.

TABLE II

| Polymer | Impregnation Medium: | |
|---|---|---|
| | Fragrance under $N_2$ pressure | Fragrance/$CO_2$ mixture* |
| Copolymer I [ethylene-vinyl acetate (9% vinyl acetate)] | 4.19% | 8.65% |
| Polypropylene | 0.20% | 1.42% |
| Polyethylene | 1.35% | 2.65% |

*9 weight percent fragrance

Table III shows the polymer characterizations of the polymers used in Examples 1 and 2 as referred to in Tables I and II.

TABLE III

The melt flow rate ($I_2$ at 230° C.) and the melt index ($I_2$ at 190° C.) in decigrams per minute (dg/minute) is determined by ASTM test method D 1238.

(1) Polypropylene—melt flow rate ($I_2$ at 230° C.) is 3.3 (dg/minute), density=0.903 g/cc.

(2) Polyethylene—melt index ($I_2$ at 190° C.) is 7.0 (dg/minute), density=0.917 g/cc.

(3) Copolymer I—melt index ($I_2$ at 190° C.) is 3.0 (dg/minute), density=0.930 g/cc [Ethylene-vinyl acetate (9% vinyl acetate)].

(4) Copolymer II—melt index ($I_2$ at 190° C.) is 150 (dg/minute), density=0.937 g/cc [Ethylene-vinyl acetate (18% vinyl acetate)].

(5) Copolymer III—melt index ($I_2$ at 190° C.) is 20.0 (dg/minute), density=0.931 g/cc [Ethylene-ethyl acrylate (18% ethyl acrylate)].

Other features, advantages, and specific embodiments of this invention will become readily apparent to those exercising ordinary skill in the art after reading the foregoing disclosures. In this regard, while specific embodiments of this invention have been described in considerable detail, variations and modifications of these embodiments can be effected without departing from the spirit and scope of the invention as disclosed and claimed.

What is claimed is:

1. A method of forming an impregnated thermoplastic polymer, comprising:
    dissolving an impregnation material in a volatile swelling agent maintained at or near supercritical conditions for the volatile swelling agent, said impregnation material being selected from the group consisting of fragrances, pest control agents and pharmaceuticals;
    swelling the thermoplastic polymer by contacting it with the impregnation material-laden volatile swelling agent at or near supercritical conditions for the volatile swelling agent; and
    reducing the pressure whereby the volatile swelling agent diffuses out of the impregnated thermoplastic polymer.

2. The method of claim 1 wherein said impregnation material is a perfume.

3. The method of claim 1 wherein said impregnation material is a fruit fragrance.

4. The method of claim 1 wherein said impregnation material is a flower fragrance.

5. The method of claim 1 wherein said impregnation material is a pest control agent.

6. The method of claim 1 wherein said impregnation material is a pharmaceutical.

7. The method of claim 1 wherein said swelling agent is carbon dioxide.

8. The method of claim 1 wherein said swelling agent is nitrous oxide.

9. The method of claim 6 wherein said pharmaceutical is scopolamine.

* * * * *